US006187925B1

(12) United States Patent
Humphrey et al.

(10) Patent No.: US 6,187,925 B1
(45) Date of Patent: Feb. 13, 2001

(54) INTERMEDIATES AND PROCESS FOR THE SYNTHESIS OF AZASTEROIDS

(75) Inventors: Guy R. Humphrey, Belle Mead; Ross A. Miller, Fanwood, both of NJ (US); Wenjie Li, Pittsburgh, PA (US)

(73) Assignee: Merck & Co., Inc., Rahway, NJ (US)

( * ) Notice: Under 35 U.S.C. 154(b), the term of this patent shall be extended for 0 days.

(21) Appl. No.: 09/212,227

(22) Filed: Dec. 16, 1998

Related U.S. Application Data

(60) Provisional application No. 60/068,536, filed on Dec. 23, 1997.

(51) Int. Cl.[7] ............... C07D 221/18; C07D 221/22; C07D 473/00; C07D 239/02; C07D 401/02
(52) U.S. Cl. .................. 546/77; 544/238; 544/276; 544/316; 544/319
(58) Field of Search .................. 546/77; 544/238, 544/276, 316, 319

(56) References Cited

U.S. PATENT DOCUMENTS

| 2,759,952 | 8/1956 | Huffman | 260/397.5 |
|---|---|---|---|
| 4,377,584 | 3/1983 | Rasmusson et al. | 424/258 |
| 4,760,071 | 7/1988 | Rasmusson et al. | 514/284 |
| 5,021,575 | 6/1991 | King et al. | 546/77 |
| 5,091,534 | 2/1992 | King et al. | 546/14 |
| 5,237,064 | 8/1993 | Bakshi et al. | 546/14 |
| 5,470,976 | 11/1995 | Humphrey et al. | 546/77 |
| 5,543,417 * | 8/1996 | Waldstreicher | 514/284 |
| 5,696,266 | 12/1997 | Humphrey et al. | 546/77 |
| 5,719,158 | 2/1998 | Durette et al. | 514/284 |
| 5,739,137 * | 4/1998 | Durette et al. | 514/256 |
| 5,910,497 * | 6/1999 | Durette et al. | 514/253 |

FOREIGN PATENT DOCUMENTS

| 0 473 225 A2 | 3/1992 | (EP) . |
|---|---|---|
| 813845 | 3/1959 | (GB) . |
| WO 90/15045 | 12/1990 | (WO) . |
| WO 95/11254 | 4/1995 | (WO) . |
| WO 95/32215 | 11/1995 | (WO) . |
| WO 97/30069 | 8/1997 | (WO) . |

OTHER PUBLICATIONS

King et al., J. Org. Chem. (1993), vol. 58, pp. 3384–3386, "Iodotrimethylsilane–mediated 2–monohalogenation of 4–aza–5alpha–androstan–3–one steroids".

Miller et al., Tet. Letters, vol. 37, No. 20, pp. 3429–3432 (1996), "A ruthenium catalyzed oxidation of steroidal alkenes to enones".

Huffman et al., J. Biol Chem., vol. 222, pp. 447–452 (1956), "16–substituted steroids: XVII. 5–androstene–3beta, 16beta–diol and 5–androstene–3beta, 16alpha–diol".

Dominguez et al., Anal. Chem., vol. 35(9), pp. 1243–1247 (1963), "Studies of the acetylation of steroids using 1–carbon–14—acetic anhydride".

* cited by examiner

*Primary Examiner*—Mukund J. Shah
*Assistant Examiner*—Brenda Coleman
(74) *Attorney, Agent, or Firm*—Catherine D. Fitch; Melvin Winokur

(57) ABSTRACT

The novel process of this invention involves the stereoselective synthesis of certain 16-substituted 4-aza-5α-androst-1-en-3-ones, and the useful intermediates obtained therein.

15 Claims, No Drawings

INTERMEDIATES AND PROCESS FOR THE SYNTHESIS OF AZASTEROIDS

CROSS REFERENCE TO RELATED APPLICATIONS

The present application claims priority of U.S. provisional application Ser. No. 60/068,536, filed Dec. 23, 1997.

BACKGROUND OF THE INVENTION

The principal mediator of androgenic activity in some target organs, e.g., the prostate, is 5α-dihydrotestosterone ("DHT"), formed locally in the target organ by the action of 5α-reductase, which converts testosterone to DHT. Certain undesirable physiological manifestations, such as acne vulgaris, seborrhea, female hirsutism, androgenic alopecia (also called androgenetic alopecia) which includes female and male pattern baldness, and benign prostatic hyperplasia, are the result of hyperandrogenic stimulation caused by an excessive accumulation of testosterone ("T") or similar androgenic hormones in the metabolic system. Inhibitors of 5α-reductase will serve to prevent or lessen symptoms of hyperandrogenic stimulation in these organs. See especially U.S. Pat. No. 4,377,584, issued Mar. 22, 1983, and U.S. Pat. No. 4,760,071, issued Jul. 26, 1988, both assigned to Merck & Co., Inc. It is now known that a second 5α-reductase isozyme exists, which interacts with skin tissues, especially in scalp tissues. See, e.g., G. Harris, et al., *Proc. Natl. Acad. Sci. USA*, Vol. 89, pp. 10787–10791 (November 1992). The isozyme that principally interacts in skin tissues is conventionally designated as 5α-reductase 1 (or 5α-reductase type 1), while the isozyme that principally interacts within the prostatic tissues is designated as 5α-reductase 2 (or 5α-reductase type 2).

U.S. Pat. No. 5,237,064 describes a process for producing 7β-substituted 5α-androstan-3-ones. U.S. Pat. No. 5,470,976 describes the stereoselective hydrogenation of the delta-5 double bond of a 17-substituted azasteroid. U.S. Pat. No. 5,120,847 and U.S. 5,021,575 relate to the insertion of a double bond at the 1,2 position of a 4-azasteroid.

The instant invention provides an improved process for the synthesis of 16-substituted 7-β-methyl-4-aza-5α-androst-1-en-3-ones. 16β-substituted 7-β-methyl-4-aza-5α-androst-1-en-3-ones are described in PCT publication WO 95/11254. Also provided by the present invention are intermediates useful in the present process.

SUMMARY OF THE INVENTION

The novel process of this invention involves the stereoselective synthesis of certain 16-substituted 4-aza-5α-androst-1-en-3-ones, and the useful intermediates obtained therein. These novel intermediates and this novel process can be exemplified in the following embodiment.

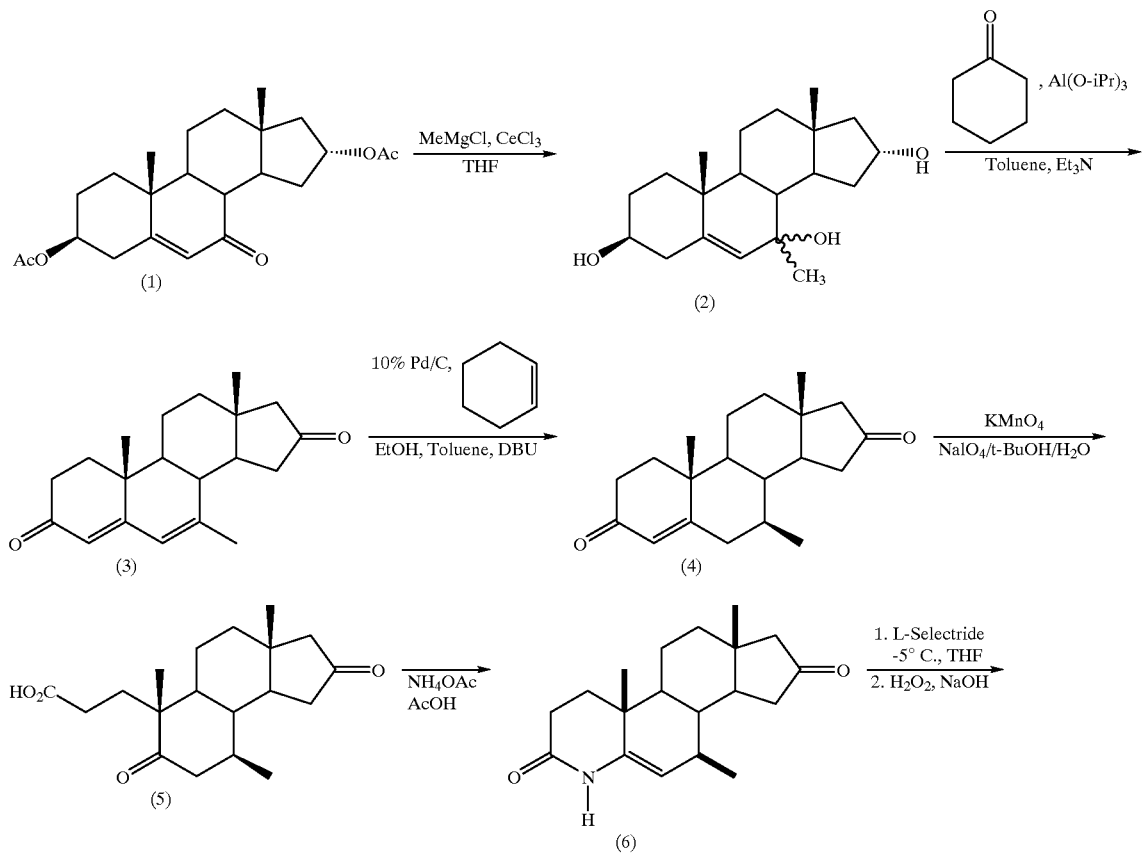

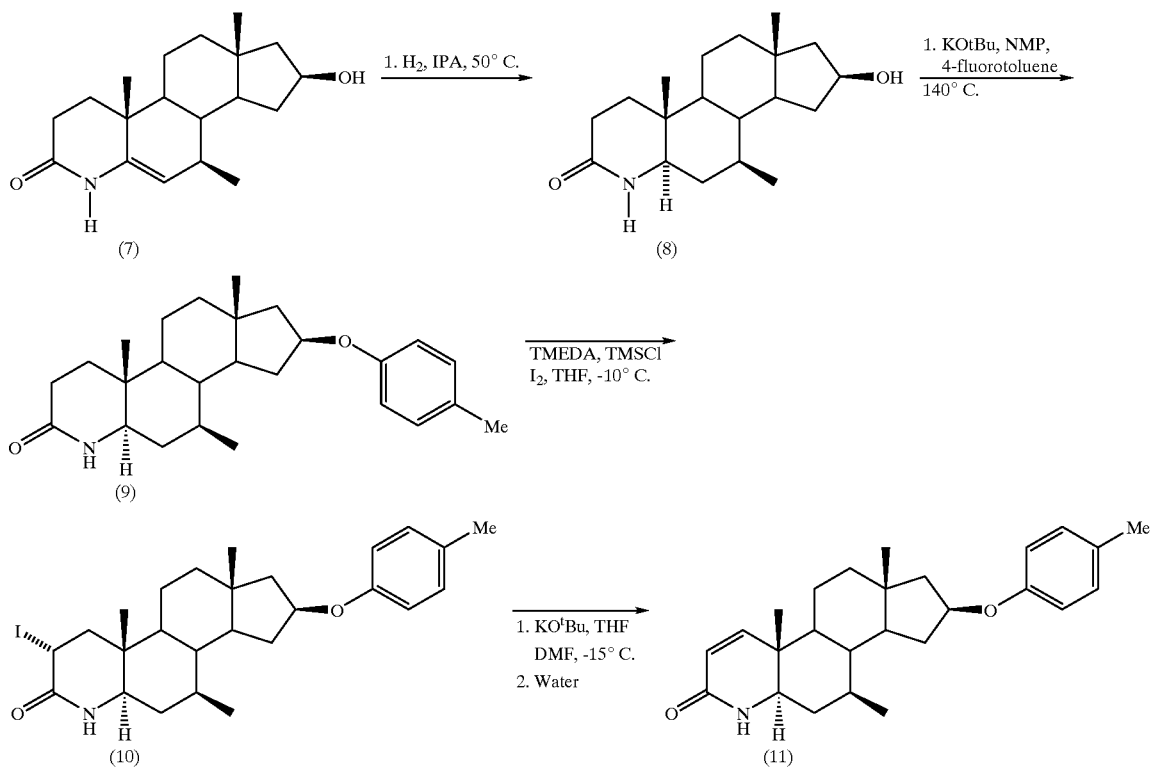

The products of the present process are useful as a inhibitors of 5α-reductase, particularly 5α-reductase type 1. 5α-reductase inhibitors are useful in the treatment of hyperandrogenic disorders such as benign prostatic hyperplasia, acne vulgaris, seborrhea, female hirsutism, androgenic alopecia (androgenetic alopecia), including male pattern baldness, and the prevention and treatment of prostatic carcinoma.

DETAILED DESCRIPTION OF THE INVENTION

A general procedure for the process of the present invention is shown below:

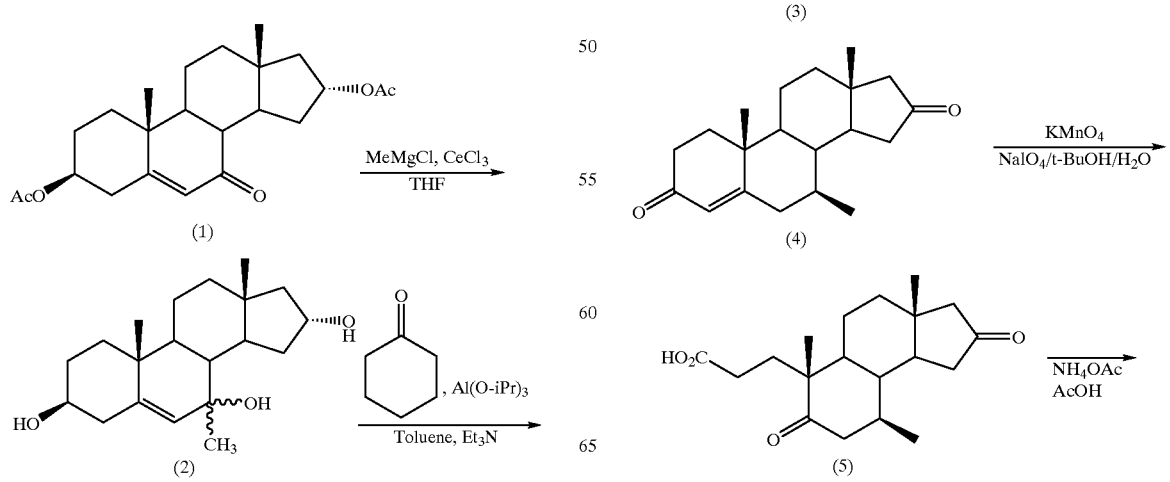

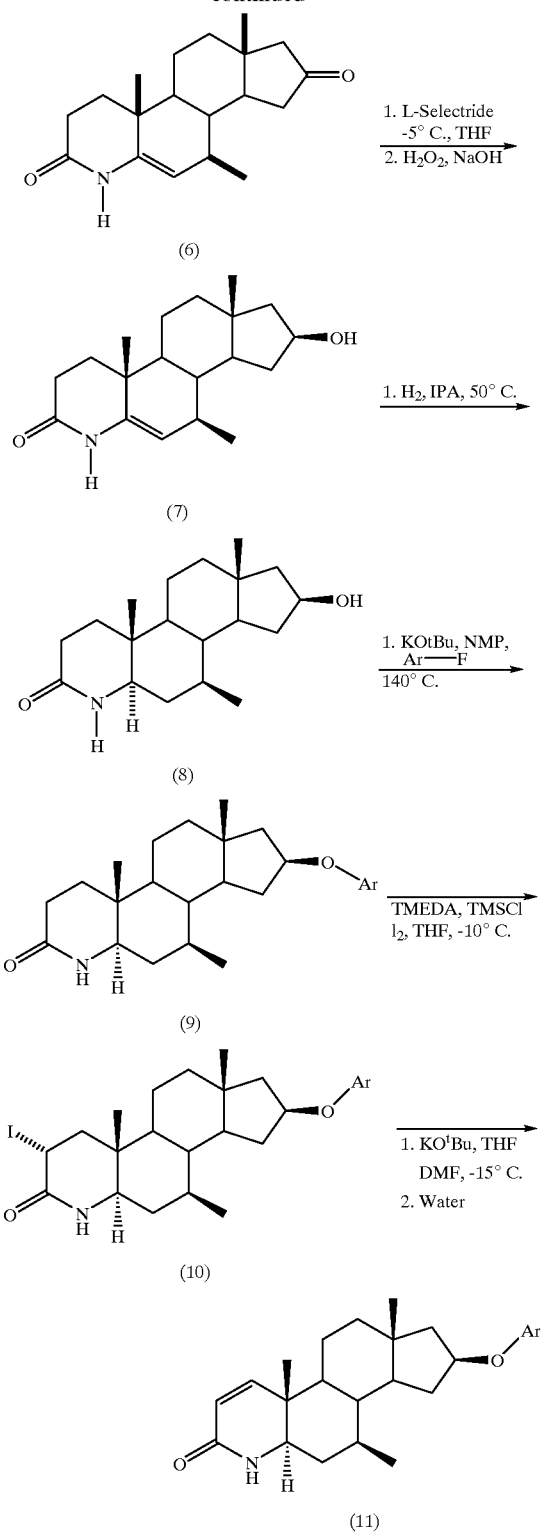

wherein Ar is:

unsubstituted or mono- or di-substituted phenyl, naphthyl, or 5, 6 or 7 membered heteroaromatic ring containing at least one member selected from the group consisting of: one ring oxygen atom, one ring sulfur atom, 1–4 ring nitrogen atoms, or combinations thereof; in which the heteroaromatic ring can also be fused with one benzo or heteroaromatic ring.

When Ar is heteroaryl, the heteroaryl ring may be attached within structural formula I or substituted on any carbon atom in the ring which results in the creation of a stable structure.

The substituents on the aryl and heteroaryl groups named above are independently selected from:

i) halo; hydroxy; cyano; nitro; mono-, di- or trihalomethyl; mono-, di- or trihalomethoxy; $C_{2-6}$ alkenyl; $C_{3-6}$ cycloalkyl; formyl; hydrosulfonyl; carboxy; ureido;

ii) $C_{1-6}$ alkyl; hydroxy $C_{1-6}$ alkyl; $C_{1-6}$ alkyloxy; $C_{1-6}$ alkyloxy $C_{1-6}$alkyl; $C_{1-6}$ alkylcarbonyl; $C_{1-6}$ alkylsulfonyl; $C_{1-6}$ alkylthio; $C_{1-6}$ alkylsulfinyl; $C_{1-6}$ alkylsulfonamido; $C_{1-6}$ alkylarylsulfonamido; $C_{1-6}$ alkyloxycarbonyl; $C_{1-6}$ alkyloxycarbonyl $C_{1-6}$alkyl; $R_bR_cN$—C(O)—$C_{1-6}$alkyl; $C_{1-6}$ alkanoylamino $C_{1-6}$ alkyl; aroylamino $C_{1-6}$ alkyl; wherein the $C_{1-6}$ alkyl moiety is unsubstituted or substituted with 1–3 of: halo; $C_{1-4}$alkoxy; or trifluoromethyl;

iii) aryl; aryloxy; arylcarbonyl; arylthio; arylsulfonyl; arylsulfinyl; arylsulfonamido; aryloxycarbonyl; wherein the aryl moiety is unsubstituted or substituted with 1–3 of: halo; $C_{1-4}$alkyl; $C_{1-4}$alkoxy; or trifluoromethyl;

iv) —C(O)NR$_b$R$_c$; —O—C(O)—NR$_b$R$_c$; —N(R$_b$)—C(O)—R$_c$; —NR$_b$R$_c$; R$_b$—C(O)—N(R$_c$)—; where R$_b$ and R$_c$ R$_b$ and R$_c$ are independently H, $C_{1-6}$ alkyl, aryl, or aryl$C_{1-6}$alkyl; wherein the alkyl moiety is unsubstituted or substituted with 1–3 of: halo; $C_{1-4}$alkoxy; or trifluoromethyl; and the aryl moiety can be substituted with 1–3 of: halo; $C_{1-4}$alkyl; $C_{1-4}$ alkoxy; or trifluoromethyl; and —N(R$_b$)—C(O)FIG.OR$_g$, wherein R$_g$ is $C_{1-6}$alkyl or aryl, in which the alkyl moiety is unsubstituted or substituted with 1–3 of: halo; $C_{1-4}$alkoxy; or trifluoromethyl, and the aryl moiety is unsubstituted or substituted with 1–3 of: halo; $C_{1-4}$alkyl; $C_{1-4}$ alkoxy, or trifluoromethyl; —N(R$_b$)—C(O) NR$_c$R$_d$, wherein R$_d$ is selected from H, $C_{1-6}$ alkyl, and aryl; in which said $C_{1-6}$alkyl and aryl is unsubstituted or substituted as described above for R$_b$ and R$_c$;

v) a heterocyclic group, wherein the heterocyclic ring can be fused with a benzo ring, and wherein said heterocyclic ring is unsubstituted or substituted with one to three substituents, as defined above for i), ii), iii) and iv), excluding v) a heterocyclic group.

Preferably, Ar is selected from: unsubstituted or mono- or di-substituted phenyl, naphthyl, pyridyl, furyl, pyrrolyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl, and benzoxazolyl.

In another embodiment, Ar is selected from: unsubstituted or mono- or di-substituted phenyl, naphthyl, pyridyl, pyrrolyl, pyrazinyl, pyrimidyl, and oxazolyl.

Preferably, the aryl and heteroaryl substituents are selected from:

vi) halo; cyano; nitro; trihalomethyl; trihalomethoxy; $C_{1-6}$ alkyl; aryl; $C_{1-6}$ alkylsulfonyl; $C_{1-6}$ alkylarylsulfonamino;

vii) —NR$_b$R$_c$; R$_b$—C(O)—N(R$_c$)—; wherein R$_b$ and R$_c$ are independently H, $C_{1-6}$ alkyl, aryl, or aryl$C_{1-6}$alkyl; wherein the alkyl moiety is unsubstituted or substituted with 1–3 of: halo; $C_{1-4}$alkoxy; or trifluoromethyl; and the aryl moiety is unsubstituted or substituted with 1–3 of: halo; $C_{1-4}$alkyl; $C_{1-4}$ alkoxy; or trifluoromethyl;

viii) a heterocyclic group, which is a 5 membered aromatic ring, containing one ring nitrogen atom, or one ring oxygen and one ring nitrogen atom.

The starting material for the process is produced according to the procedures in Miller et al., Tetrahedron Letters 37(20) 3429–3432 (1996) and those in PCT publication WO 95/32215, and is generally known and available in the art.

Addition of methyl magnesium chloride to the 7-keto-3, 16 bis acetate starting material (1) cleaves the 3 and 16 acetates with concurrent addition to the 7-ketone to produce (2). Anhydrous cerium trichloride, in the proper needle form, was added to the Grignard before addition to the 7-ketone and improved the yield of the reaction by >15%. The triol (2) can be carried on to the next step without purification, or it may be isolated.

Oxidation of the triol (2) to the dienedione (3) was carried out under Oppenauer conditions with 2-butanone, aluminum isopropoxide, and triethylamine. Concurrent hydrolysis of the aluminum salts and elimination of the 7-OH occurred upon aging with concentrated HCl. Butanone dimers can be removed from the reaction mixture by a water distillation before carrying on to the next step, or the dienedione (3) may be isolated.

A chemo- and stereoselective reduction of the dienone (3) to the 7-P methyl enone (4) was achieved under transfer hydrogenation conditions using 10% Pd/C and cyclohexene as the hydrogen donor. Careful front run of the reaction and frequent monitoring ensured little overreduction and a high yield of enone.

The oxidative cleavage of the enone (4) to the seco acid (5) was carried using sodium periodate and catalytic potassium permangante with sodium carbonate.

Introduction of the nitrogen atom into the A ring occurs in refluxing acetic acid with ammonium acetate. BHT was added as a radical inhibitor to prevent decomposition of enelactam ketone(6).

Chemo- and stereoselective reduction of the crude enelactam ketone (6) was carried out with L-Selectride at −5° C. After an oxidative workup to convert the trialkylboron by-products to boric acid, the enelactam alcohol (7) is crystallized from acetonitrile. Running this reaction under more dilute conditions and reducing the level of toluene improves yield.

Hydrogenation of the enelactam alcohol (7) is critical because enelactam left behind does not crystallize away from the NH lactam alcohol (8) and impacts on the purity of the final product.

Arylation of the NH lactam alcohol (8) was carried out using potassium t-butoxide in N-methyl-pyrrolidinone to give (9). The isomeric purity of the fluoro-substituted aryl reagent is of key concern in this reaction because both the ortho and meta isomers of the fluorotoluene also react to give the corresponding isomeric products.

Complete iodination in forming (10) is important since the NH lactam alcohol is not easily removed from the iodide or final bulk drug by recrystallization. The level of NH lactam alcohol in the iodide is typically controlled at less than 0.2 wt %. Care must be taken to carry out the quench at low temperature (less than 5° C.) in order to avoid reduction of the iodide to the starting material.

Formation of the 1,2-double bond by dehydroiodination forms the product (11).

Representative experimental procedures utilizing the novel process are detailed below. These procedures are exemplary only and should not be construed as being limitations on the novel process of this invention.

Abbreviations: ACN is acetonitrile; BHT is 2,6-t-butyl-4-methylphenol; ca is circa; DBU is (1,8-diazabicyclo[5.4.0] undec-7-ene; IPA is isopropyl alcohol; L-Selectride® is lithium tri-sec-butylborohydride; MEK is methyl ethyl ketone; NMP is 1-methyl-2-pyrrolidinone; THF is tetrahydrofuran; TMEDA is N,N,N',N'-Tetramethylethylenediamine; TMSCl is chlorotrimethylsilane.

EXAMPLE 1

Preparation of 3,6,16-Triol (2)

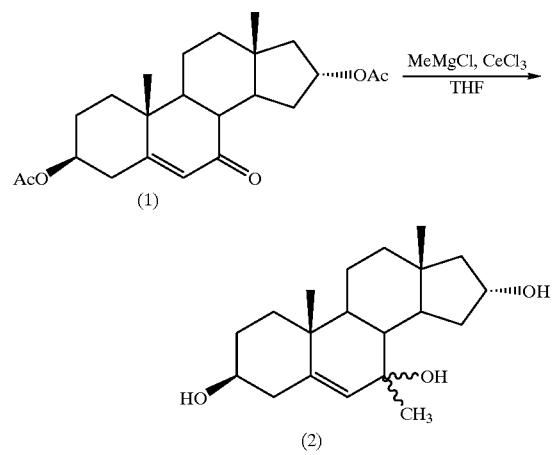

Cerium chloride (3.96 kg) was charged as a solid to the reaction vessel. THF (35 kg) was charged using vacuum, then water (20 mL) was added via the charge port and the mixture aged at 35° C. for 1 hr. A sample was taken and examined by microscopy to ensure that conversion to the required crystal form had occurred. (Amorphous cerium chloride stirred in THF converts to a fine rod-like crystalline form. This crystalline form is necessary to obtain the stereoselectivity in the Grignard reaction. Previous experience had shown that the water content of the THF/cerium chloride should be less than 1000 ppm in order to get the required crystal form. Wetter slurries were found to irreversibly form another crystal form that did not exhibit the same specificity in the Grignard reaction. However, the THF used in this instance was extremely dry (<50 ppm) and stirring the amorphous cerium chloride in it did not produce the required conversion and the solid remained amorphous. It was demonstrated that a small amount of water is necessary for the conversion to take place, and water was added to the batch to give a total water content of ca 500 ppm.) After cooling the batch to 25° C., 3M methyl magnesium chloride in THF (80.46 kg) was added to the vessel. The mixture was cooled to 0–5° C. and aged for 30 minutes. The 7-ketone starting material (1) (9.2 kg) was slurried in THF (50 L) and added to the Grignard reagent slurry over 75 minutes, maintaining a temperature of <20° C.

The batch was sampled and reaction completion confirmed by HPLC: <0.1A % (1) detected. The Grignard reaction mixture was slowly added to a quenching solution formed by the addition of toluene (70 kg) to a solution of water (146 L) and solid citric acid (43.9 kg). Care was made to maintain the temperature at <20° C. The reaction vessel and transfer lines were rinsed with THF (10 kg).

The mixture was stirred for 15 minutes then settled for 30 minutes. Both phases were cut to drums and the aqueous layer returned to was back extracted with 39 kg of ethyl acetate (agitated for 10 mins, settled for 30 mins). The aqueous layer was cut to waste drums and the THF batch layer was combined with the ethyl acetate layer. 20% sodium carbonate solution (49.2 kg) was added to the stirred solution over 15 minutes then the mixture settled for 30 minutes and the aqueous phase cut to waste.

The batch layer was washed with 51.5 kg of 20% sodium chloride solution (agitated for 10 mins, settled for 30 minutes) and the aqueous phase cut to waste. Triethylamine (4.8 kg) was added and the solution concentrated in vacuo to ca 100 L. Toluene was added and distillation continued, until the level of THF/ethyl acetate had dropped to <0.5vol % by GC. The final volume was made up to 275 L, with toluene and the slurry held was used in Example 2.

| HPLC Conditions: | |
| --- | --- |
| Column | YMC J-Sphere ODS H80 250 × 4.6 mm I.D. |
| Eluent A | ACN |
| Eluent B | Unbuffered water |
| Gradient | 30% A to 80% A in 25 min; hold for 5 min |
| Inj vol | 20 µl |
| Detection | UV at 200 nm |
| Flow | 1.5 ml/min |
| Column temp | 35° C. |
| Sample preparation | 100x dilution with acetonitrile; waste aq layers diluted 50x |
| Compound | Retention Times | Response Factor(area counts/wt) |
| Triols | 4.6, 6.4 | 0.71 |
| 7-ketone | 14.6 | 1 |
| Toluene | 16.4 | |
| BHT | 29.5 | |
| GC conditions | | |
| Column | Chrompack plot fused silica 25m × 0.53 mm | |
| coating | poraplot Q | |
| Oven temperature | 250° C. Isothermal | |
| Inj temp | 275° C. | |
| Det temp | 275° C. | |
| Sample preparation | 40x dilution with MeOH | |
| Compound | Retention | Relative Response Factor |
| MeOH | 2.0 min | |
| THF/EtOAc | 2.8,3.2 min | 1 |
| Toluene | 4.5 min | 1.5 |

EXAMPLE 2

Preparation of Diene-Dione (3)

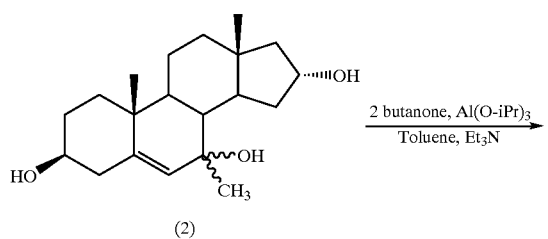

To a slurry of triol in toluene (7.59 kg in 275 L) was added triethylamine (3.8 kg) and aluminium isopropoxide (10 kg) followed by 2-butanone (100 kg). The mixture was heated at reflux for 6 hrs, cooled slightly, a sample was taken, and reaction completion confirmed by HPLC(<5A % 16-OH's dienone relative to 16-keto-diene-dione). The batch was cooled to 20° C., then allowed to stand overnight.

A mixture of water (62.5 L) and 12N hydrochloric acid (73.7 kg) was transferred to the reaction mixture. The reaction mixture was heated to 58–60° C. and aged for 4 hrs. A sample was taken and the disappearance of 7-OH enone intermediate confirmed by HPLC. The batch was cooled to 20° C., allowed to settle for 15 mins and the aqueous phase cut to waste.

2.5% sodium bicarbonate solution (100 L) was added to the toluene layer, stirred for 15 mins, settled for 30 mins and the aqueous phase cut to waste. This procedure was repeated with 100 L of water.

The organic phases from the two batches prepared as described above were combined and concentrated in vacuo to a volume of 100 L. Water was fed in under vacuum then distillation continued at atmospheric pressure until the level of 2-butanone dimers in the batch had dropped to <3A % relative to diene-dione; a total of 70 L of water was distilled. Toluene (100 L) was added to the residue, the mixture agitated for 5 mins then settled for 15 mins. The organic layer was saved. The aqueous phase returned was extracted with toluene (40 L). The organic layers were combined and concentrated in vacuo to a final volume of ca 60 L. The solution was held for Example 3.

| HPLC Conditions | |
| --- | --- |
| Column | YMC J-Sphere ODS H80 250 × 4.6 mm I.D. |
| Eluent A | ACN |
| Eluent B | Unbuffered water |
| Gradient | 30% A to 80% A in 25 min; hold for 5 min |
| Flow | 1.5 ml/min |
| Inj vol | 20 µl |
| Detection | UV at 200 nm for triols, 240 nm for 7-OH enone |
| MEK by-product | and removal, 290 nm for dienone assays |
| Column temp | 35° C. |
| Sample preparation | 100x dilution with acetonitrile; waste aq layers diluted 25–50x |
| Compound | Retention Times | 1 |
| Triols | 4.6, 6.4 | 200 nm |
| 7-OH enone | 6.6 | 240 nm |
| Dienedione | 13.1 | 290 nm |
| Toluene | 16.4 | 200 nm |
| BHT | 29.5 | 200 nm |

EXAMPLE 3

Preparation of Enone (4)

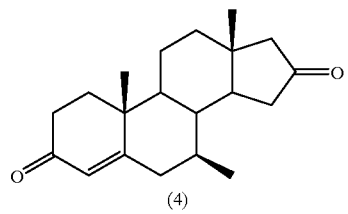

(4)

Diene-dione (3) (12.9 kg) was converted to enone (4) (11.69 assay kg, 90.0% yield) in one batch. The enone was not isolated but carried through for use in Example 4 as a solution in t-butanol.

To the reaction vessel was added 10% Pd/C (5.32 kg, 51.5% water wet), followed by the toluene solution of diene-dione obtained as a product of Example 2, (12.9 kg in 70 L), ethanol (38.1 L), and cyclohexene (64.9 L). The mixture was agitated and DBU (1.28 kg) was added.

A sample was taken and the mixture warmed to reflux. The reaction was sampled periodically and heating continued (6 hrs) until the diene-dione level, measured by HPLC fell below 1.0 mg/ml. (As benzene is produced as a by-product of the reaction, care was taken to use local extraction when sampling.) After cooling to 25° C., the batch was filtered through a 45 cm plate filter set with a polypropylene cloth, card, and Solka Floc diatomaceous earth (1.5 kg).

The filter became blocked after about 50% of the slurry had passed through and had to be dismantled and reset.

The vessel, lines and filter pad were rinsed with toluene (20 L) and the combined filtrates allowed to stand overnight. 1N hydrochloric acid (44 L) was added to the filtrate. The mixture was agitated for 5 mins, settled for 15 mins and the lower aqueous phase cut to waste. This wash procedure was repeated with 5% sodium chloride solution (42 L).

The organic phase was concentrated in vacuo to ca 50 L then transferred to a reaction vessel via a 0.5 m cotton cartridge filter and distillation continued to ca 22 L. The solvent was switched to t-butanol. t-Butanol (total of 144 kg) was charged and distilled in vacuo (30 L distilled) until the required removal of the previous solvents was achieved (toluene <15 mg/ml, cyclohexene, 0.05 mg/ml). The batch (11.69 kg of enone in 136.2 kg of solution) was held for further reaction in Example 4. (Because t-Butanol freezes at 26° C., all drums of pure solvent and batch solutions were stored on a heating pad to maintain a temperature of ca 40° C.)

| HPLC Conditions | |
|---|---|
| Column | Zorbax SB Phenyl 250 × 4.6 mm I.D. |
| Eluent A | ACN |
| Eluent B | Aqueous 0.1 v/v% $H_3PO_4$ |
| Gradient | 30% A to 80% A in 25 min; hold for 5 min |
| Flow | 1.5 ml/min |
| Inj vol | 20 μl |
| Detection | UV at 192 nm (benzene, cyclohexene), 245 nm (enone), 295 nm(dienone) |
| Column temp | 35° C. |
| Sample preparation | 100x–1000x dilution with acetonitrile; waste aq layers diluted 10x–25x (non-linearity for dienedione, enone) |
| Compound | Retention Times |
| Benzene | 7.7 |
| Toluene | 10.0 |

| | |
|---|---|
| Cyclohexene | 10.9 |
| Dienedione | 13.9 |
| Enone | 14.9 |

EXAMPLE 4
Preparation of Seco acid (5)

Enone (4) (11.69 assay kg) was converted to seco acid (10.3 assay kg) in 83% yield in two batches. The product was not isolated but held as a solution in ethyl acetate for Example 5.

The oxidizing solution was made up first. Water (150 L), sodium periodate (25.54 kg) and potassium permanganate (0.47 kg) were added to the reaction vessel and the mixture warmed to 65° C. until all the solids had dissolved (ca 30 minutes).

A solution of enone (4) (5.9 kg) in t-butanol (70 kg) was added to a second reaction vessel and rinsed in with t-butanol (16 kg). A solution of sodium carbonate (2.10 kg) in water (80 L) was added to the enone solution and stirred at 55° C. The oxidant was added over 1 hr, maintaining the temperature at 60° C.

The batch was aged at 60° C. for 30 mins then sampled and assayed for starting material (0.07 mg/ml, 99% complete), and then heated at 80° C. for 30 mins to decompose excess oxidant. The resulting brown slurry was cooled to 12–15° C., aged for 15 mins then filtered through a 65 cm filter fitted with a polypropylene cloth. The vessel and filter pad were rinsed with aqueous t-butanol (water 70 L, t-butanol 35 L). The filter removed the bulk of the inorganic solids but some fine brown material passed through.

The liquors were returned to the reaction vessel via a 0.5 m cotton cartridge filter, then the pH of the solution was measured at 9. The cartridge filter became blocked with the fine brown inorganic solid and required changing several times during the transfer. If the pH had been <9, it would have been adjusted by addition of sodium carbonate solution.

Hexane (30 kg) was added. The mixture was agitated for 15 minutes, settled for 15 mins then the aqueous layer cut to drums and the hexane layer cut to waste. The aqueous phase was returned to the reaction vessel together with ethyl acetate (41 kg), then the pH of the batch adjusted to 1–2 by addition of 12N hydrochloric acid solution, maintaining the temperature at 15–20° C. The mixture was stirred for 15 mins, settled for 30 mins and both phases cut to plastic lined drums. The aqueous phase was returned to the vessel and extracted with ethyl acetate (26 kg). This extraction was repeated, and then all the organic phases combined in the reaction vessel, and washed with 10% brine solution (27 L). The aqueous phase was cut to waste and the organic phase drummed and assayed.

| HPLC Conditions | |
| --- | --- |
| Column | Zorbax SB Phenyl 250 × 4.6 mm I.D. |
| Eluent A | ACN |
| Eluent B | Aqueous 0.1 v/v% $H_3PO_4$ |
| Gradient | 30% A to 80% A in 25 min; hold for 7 min |
| Flow | 1.5 ml/min |
| Inj vol | 20 µl |
| Detection | UV at 192 nm (seco acid), 245 nm (enone) |
| Column temp | 35° C. |
| Sample preparation | 100x dilution with acetonitrile; waste aq, hexane layers diluted 10x–25x |
| Compound | Retention Times |
| Acetic acid | 2.1 |
| Ethyl acetate | 3.6 |
| Seco acid | 8.1 |
| Toluene | 10.0 |
| Enone | 14.9 |

EXAMPLE 5
Preparation of Enelactam Ketone (6)

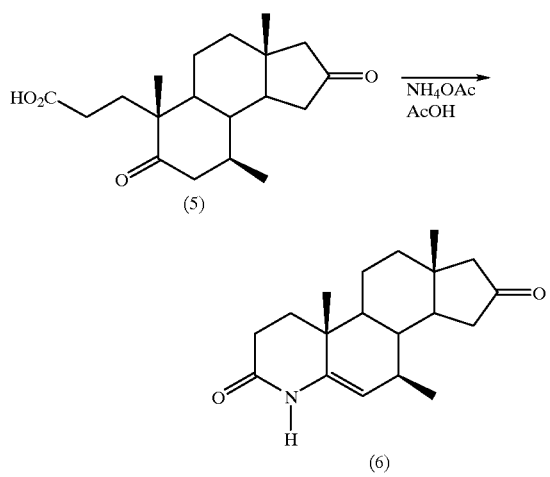

Seco-acid (9.8 kg) was converted to ene lactam ketone (9.07 kg) in a single batch. The product was not isolated, but instead carried through to Example 6 as a toluene solution.

A solution of seco-acid (10.3 kg) in ethyl acetate (282 kg) was added to a reaction vessel and concentrated in vacuo to a minimum stirred volume of ca 35 L. The solvent was then switched to acetic acid in vacuo. A total of 80 kg of acetic acid was added, and 60 L distilled to achieve an ethyl acetate concentration of <1mg/ml in a final volume of 76 L (seco-acid concentration: 124.9 g/L). A portion of this solution (4 L, containing 500 g of seco-acid) was removed for other studies.

The remaining solution (9.8 kg in 72 L) was diluted with acetic acid to a total volume of 150 L, then BHT (0.1 kg) and ammonium acetate (23.7 kg) were added via the charge port and the mixture warmed to reflux. Acetic acid (60 L) was distilled and then reflux continued for a total of 5 hrs. The progress of the reaction was monitored by HPLC and the reaction was considered complete when the concentration of seco-acid fell to <0.5 mg/ml.

The batch was cooled to 20° C., then toluene (100 L) and water (100 L) added, the solution stirred for 20 mins, settled for 20 mins and both phases cut to plastic lined drums. The aqueous phase was returned to the reaction vessel and extracted with toluene (50 L). The organic phases were combined, washed with 5% aqueous sodium chloride solution (50 L) and assayed (total volume 160 L, 56.7 g/L for 98.5% yield). The solution was concentrated in vacuo to give a thick slurry (37 L) of ene-lactam ketone.

| HPLC Conditions | |
| --- | --- |
| Column | Zorbax SB Phenyl 250 × 4.6 mm I.D. |
| Eluent A | ACN |
| Eluent B | Aqueous 0.1 v/v% $H_3PO_4$ |
| Gradient | 30% A to 80% A in 20 min; hold for 15 min |
| Flow | 1.5 ml/min |
| Inj vol | 20 µl |
| Detection | UV at 192 nm (seco acid), 240 nm (enelactam) |
| Column temp | 35° C. |
| Sample preparation | 100x dilution with acetonitrile; waste aq layers diluted 25x |
| Compound | Retention Times |
| Acetic acid | 2.1 |
| Ethyl acetate | 3.5 |
| Seco acid | 8.5 |
| Toluene | 9.4 |
| Enelactam ketone | 9.9 |
| BHT | 17.1 |

EXAMPLE 6
Preparation of Enelactam Alcohol (7)

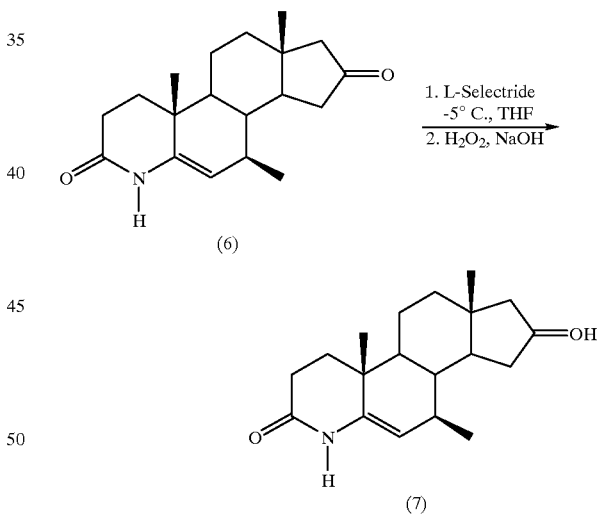

The slurry of ene-lactam ketone (9.07 kg) in toluene (35 L) in the reaction vessel was diluted with THF (89 kg) and cooled to −5° C. L-Selectride (34.5 kg of 1M solution) was added to the slurry over 1 hr, maintaining the temperature between −5° C. and 0° C. The batch was aged at 0° C. for 20 mins then sampled. HPLC analysis showed that 11.7 mol % still remained. Further L-Selectride (3.4 kg) was added then aged for 40 minutes at 0° C. and sampled. HPLC analysis showed that 9.9 mol % still remained.

The reaction was quenched by addition of 20% aqueous sodium hydroxide solution (37.4 kg), maintaining the temperature at <20° C., followed by 27% hydrogen peroxide (19.8 kg) at <30° C. The mixture was stirred at 15–20° C. for 1 hr then excess peroxide confirmed using a Merckoquant test strip (E. Merck).

The nitrogen purge rate was increased to 15 L/min during the hydrogen peroxide addition.

10% aqueous sodium sulfite solution (129 kg) was added, and the batch aged for 15 mins. The absence of peroxide was confirmed, and then the batch was settled for 15 mins and the aqueous phase cut to waste. 10% aqueous sodium chloride solution (58 kg) was added, the mixture agitated for 5 mins, settled for 15 mins and the aqueous phase cut to waste. The brine wash was repeated.

The organic phase (128.3 kg) was transferred to another reaction vessel via a 0.5 m cotton cartridge filter. The batch was concentrated to ca 40 L at atmospheric pressure then the solvent was switched to acetonitrile. A total of 200 kg of acetonitrile was charged and the mixture distilled to a final volume of 65 L. A sample was taken and toluene level (spec-200 mg/ml, measured-0.7 mg/ml) and KF(spec-400 mg/L, measured-73 mg/L) measured.

The batch was allowed to cool to room temperature slowly overnight with gentle agitation, and then cooled to 5° C. over 1 hr and aged for 30 minutes. The solid was collected on a 33 cm stainless steel filter, washed with acetonitrile, then dried at ambient temperature in vacuo overnight. The dry solid was bagged.

| HPLC Conditions: | |
|---|---|
| Column | Zorbax SB Phenyl 250 × 4.6 mm I.D. |
| Eluent A | ACN |
| Eluent B | Aqueous 0.1 v/v% H$_3$PO$_4$ |
| Gradient | 30% A to 80% A in 20 min; hold for 15 min |
| Flow | 1.5 ml/min |
| Inj vol | 20 μl |
| Detection and | UV at 240 nm (enelactam ketone, enelactam alcohol) 200 nm (BHT, toluene) |
| Column temp | 35° C. |
| Sample preparation | 100x dilution with acetonitrile; waste aq layers, filtrate and washes diluted 25x |
| Compound | Retention Times |
| Enelactam 16-β alcohol | 8.7 |
| Toluene | 9.5 |
| Enelactam ketone | 9.9 |
| BHT | 17.1 |

EXAMPLE 7

Preparation of Lactam Alcohol (8)

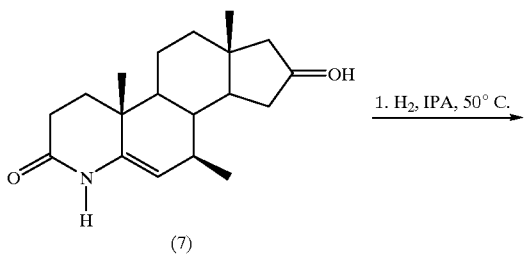

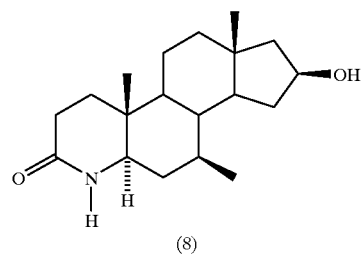

Ene-lactam alcohol (750 g) was dissolved in a mixture of IPA (10 L) and water (1.6 L) by warming to 30–40° C. in a 20 L flask. BHT(3 g) and 50% wet 10%Pd/C (375 g) was added and the mixture charged using vacuum via the dip-leg to a 20 L autoclave, and then rinsed in with IPA (1 L). The slurry was stirred under an atmosphere of hydrogen (60 psig) at 50° C. for 6 hours then at 68° C. for 16 hrs. The batch was sampled via the dip-leg and checked for completion by HPLC (spec<0.05A % starting material). If the end point had not been reached, stirring under hydrogen was continued.

The hydrogenation was carried out at 50° C. for the first few half-lives and then warmed to 68° C. Meeting the end of reaction specification is important as ene-lactam alcohol is carried through to the final product.

The batch was cooled to 30–40° C., flushed with nitrogen several times, then transferred from the autoclave and filtered through Solka Floc (1 kg). The autoclave and filter pad were washed with 1:10 water/IPA (2 L), and the combined filtrates stored.

The procedure above was repeated 10 times and the 10 batches of filtrate were combined and concentrated at atmospheric pressure to a volume of ca 25 L. After cooling to room temperature, water (42 L) was added over 45 minutes and the batch cooled to 5° C. and aged for 1 hr. The solid was collected on a 33 cm filter fitted with a polypropylene cloth and then washed with 4:1 water/IPA (10 L). The damp solid was transferred to trays and dried in vacuo at 35° C. overnight to give the lactam alcohol (8).

EXAMPLE 8

Preparation of Aryl-NH-Lactam (9)

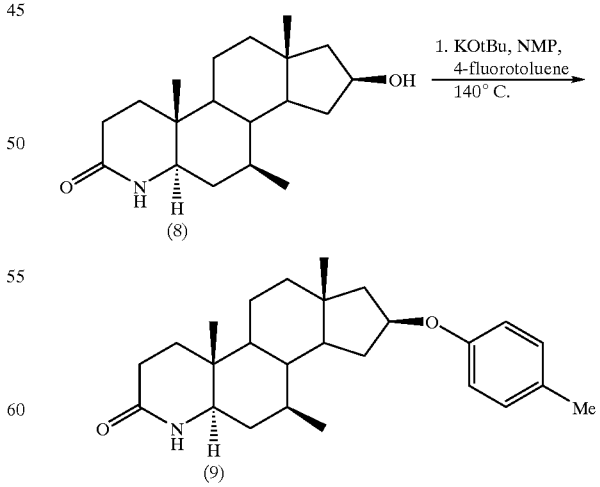

To the lactam-alcohol (8)(3.1 kg) in NMP (46.5 L) at 20° C. was added KOtBu (4.74 kg). The mixture was aged at 200C for 20 min. 4-Fluorotoluene (2.21 kg) was added in one portion. The slurry was heated to 140° C. until less than 0.5A % starting material remained by HPLC analysis.

Sample preparation, 100 L diluted to 10 ml with ACN

| HPLC Conditions: | |
|---|---|
| Column | YMC JSphere ODS 80H 4.6 mm × 25 cm |
| Eluent A | CH$_3$CN |
| Eluent B | Aqueous 0.1 M H$_3$PO$_4$ |
| Gradient | 50% A ramp to 80% A over 7 min hold for 33 min. |
| Flow rate | 1.2 ml/min |
| Inj vol | 20 μl |
| Detection | UV at 200 nm. |
| Temp 20° C. | |
| Retention times: | NH Lactam 3.3 min |
| | Fluorotoluene 9.2 min |
| | ANHL 22.1 min |
| | Ortho isomer 24.2 min |
| | Meta isomer 21.4 min |
| | 16-Alpha isomer 19.0 min |
| | 5-Beta isomer |

The reaction mixture was cooled to 20° C. and water (46.5 L) was added over 1h maintaining temperature 20–30° C. The slurry was stirred at 20° C. for 1 h.

The slurry was filtered, washed with water (10 L) and dried using nitrogen stream overnight.

EXAMPLE 9

Preparation of Aryl-NH-Iodo-Lactam (10)

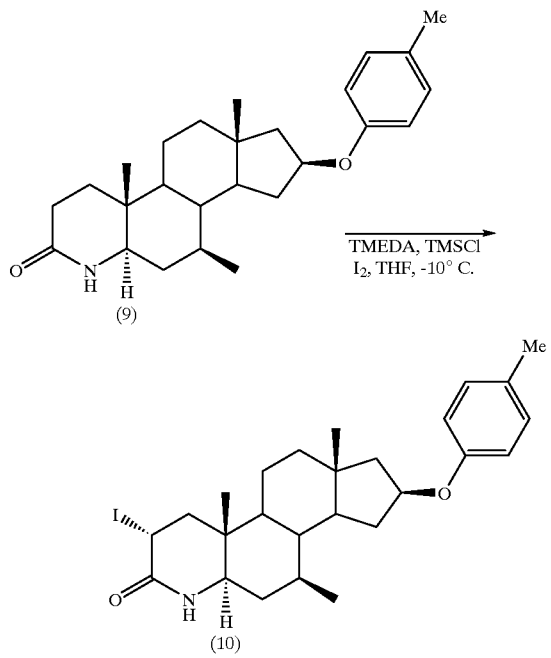

To a solution of arylated NH lactam (9) (3.3 kg) in THF (66 L) at −5° C. was added TMEDA (3.76 L) and TMSCl (2.64 L). The white slurry was stirred at −5° C. for 15 minutes. Iodine (4.24 kg) was added to the slurry in three portions over 20 min.

| HPLC Conditions for Reaction: | |
|---|---|
| Column | Zorbax SB Phenyl 4.6 mm × 25 cm |
| Eluent A | CH$_3$CN |
| Eluent B | Aqueous 0.1 M H$_3$PO$_4$ |
| Isocratic | 70% A, 30% B |
| Inj vol | 20 μl |
| Detection | UV at 200 nm. |
| Temp 20° C. | |
| Retention times: | Iodolactam 8.2 |
| | Arylated NHL 10.5 |

The reaction mixture was stirred at 0° C. for 3h until lactam SM was less than 0.1A % vs product (200 nm). The reaction mixture was cooled to −10° C. and a cold (50C) freshly prepared solution of sodium sulfite in water (1.65 kg in 33 L) was added to the reaction mixture over 20 min maintaining the quench temperature <5° C.

A color change to pale yellow from dark brown was observed.

The mixture was seeded with iodide (10 gm) and water (66 L) added over 1 h at 5° C. The resultant slurry was aged at 5° C. for 1 h.

The slurry was filtered, washed with water (33 L) and dried in a nitrogen stream on the filter finnel overnight to yield pure (10).

EXAMPLE 10

Preparation of 4-aza-7β-methyl- 16β-(4-methylphenoxy)-5α-androst-1-en-3-one(11)

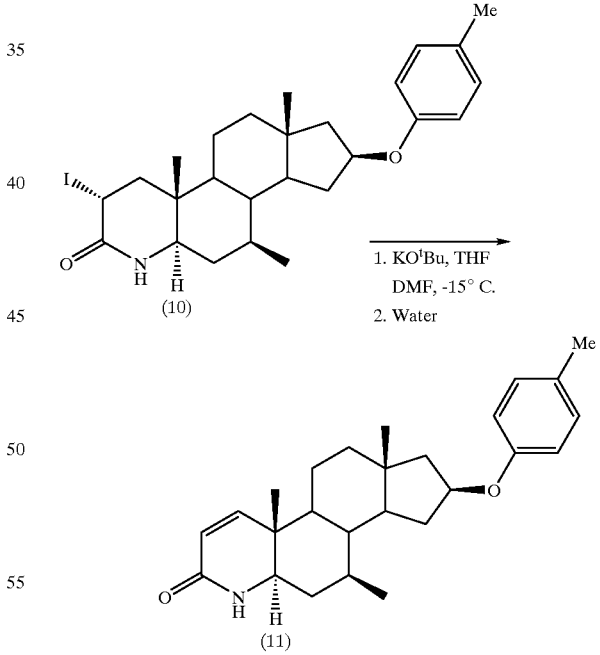

To a solution of potassium t-butoxide (6.8 kg) in dry DMF (19.8 L) at −15° C. under a nitrogen atmosphere was added a slurry of iodo-lactam (3.95 kg) in dry THF (19.8 L) over approx 1 h. THF (1 L) was used as vessel and line rinse. The reaction temperature was maintained <−15 to −10° C. during addition.

After a 15 min age a sample was taken for analysis by HPLC.

| HPLC Conditions: | |
|---|---|
| Column | Zorbax SB Phenyl 4.6 mm × 25 cm |
| Eluent A | CH$_3$CN |
| Eluent B | Aqueous 0.1 M H$_3$PO$_4$ |
| Isocratic | 70% A, 30% B |
| Inj vol | 20 μl |
| Detection | UV at 200 nm. |
| Temp 20° C. | |
| Retention times: | Iodolactam 8.2 |
| | (11) 8.9 |
| | Arylated NHL 10.2 |

Water (45 L) was added over 20 min maintaining the temperature <10° C. The resultant slurry was aged at 5° C. for 2 h. The slurry was filtered and washed with water (15 L). The cake was dried in air to <15 wt % water.

The wet cake was dissolved in THF (30 L) at room temperature and filtered through a 5 micron in-line filter into a 50 L vessel. The glassware and line were washed with THF (1 L). The filtrates were concentrated at reduced pressure to about 10 L. N-Butyl acetate (20 L) was added and concentration continued at atmospheric pressure to a final volume of about 10 L.

The hot (120° C.) solution was cooled to 80° C. and seeded with product (11) (2 gm). The resultant slurry was aged at 80° C. for 30 min then cooled to −5° C. over 2 h.

The slurry was filtered and the cake washed with cold n-butyl acetate (1 L) and dried in a nitrogen stream overnight.

EXAMPLE 11

According to the procedures outlined in Examples 1–10, the following compounds of structural formula below are prepared

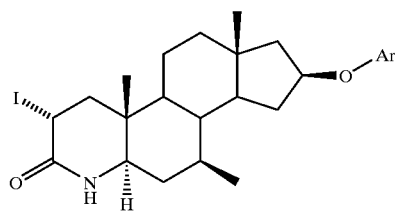

(11)

| Compound | Ar |
|---|---|
| 12 | phenyl |
| 13 | 4-chlorophenyl |

While the foregoing specification teaches the principles of the present invention, with examples provided for the purpose of illustration, it will be understood that the practice of the invention encompasses all of the usual variations, adaptations, and modifications, as come within the scope of the following claims and its equivalents.

What is claimed:
1. A process for producing a compound of structural formula (11):

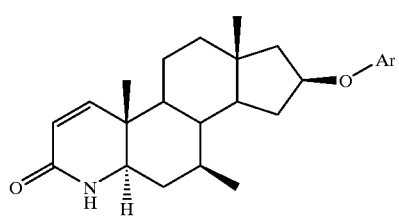

(11)

wherein:
Ar is an unsubstituted or mono- or di-substituted phenyl, naphthyl,or 5, 6 or 7 membered heteroaromatic ring containing at least one member selected from the group consisting of: one ring oxygen atom, one ring sulfur atom, 1–4 ring nitrogen atoms, or combinations thereof; in which the heteroaromatic ring can also be fused with one benzo or heteroaromatic ring;
produced by:
treating a compound of structural formula (10):

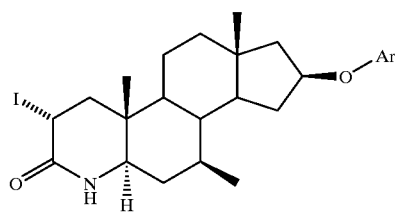

(10)

with potassium t-butoxide, and isolating the resulting product (11).

2. The process of claim 1 additionally comprising the step of producing a compound of structural formula (10):

(10)

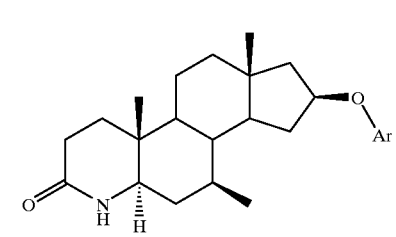

by treating a compound of structural formula (9):

(9)

with trimethylsilyl chloride in the presence of an organic base and adding iodine, and isolating the resulting product (10).

3. The process of claim 2 additionally comprising the step of producing a compound of structural formula (9):

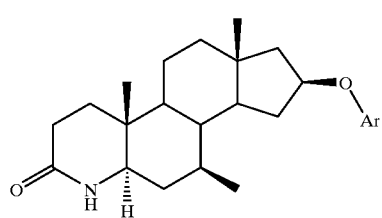
(9)

by treating a compound of structural formula (8):

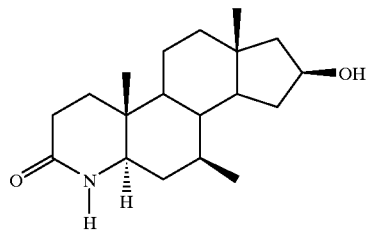
(8)

with potassium t-butoxide and adding Ar-F, and isolating the resulting product (9).

4. The process of claim 3 additionally comprising the step of producing a compound of structural formula (8):

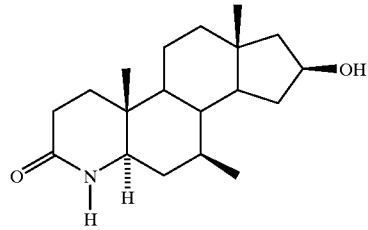
(8)

by hydrogenating a compound of structural formula (7):

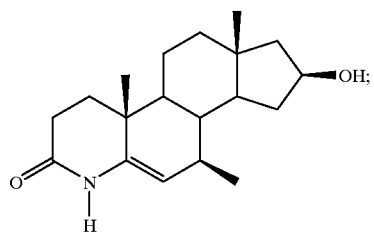
(7)

and isolating the resulting product (8).

5. The process of claim 4 additionally comprising the step of producing a compound of structural formula (7):

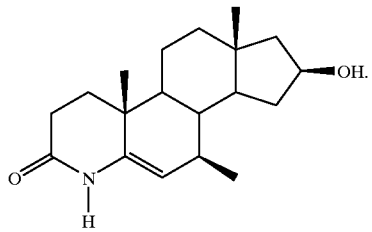
(7)

by treating a compound of structural formula (6):

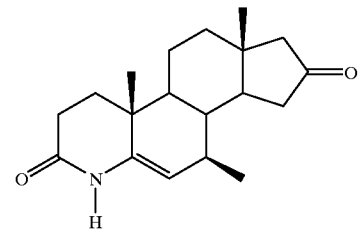
(6)

with lithium tri-sec-butylborohydride, followed by an oxidative workup, and and isolating the resulting product (7).

6. The process according to claim 5, additionally comprising the step of producing a compound of structural formula (6):

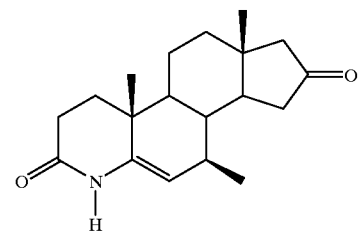
(6)

by treating a compound of structural formula (5):

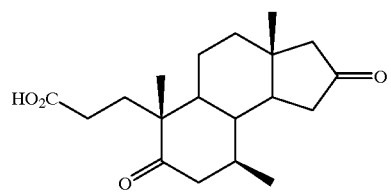
(5)

with ammonium acetate in refluxing acetic acid, and isolating the resulting product (6).

7. The process according to claim 6, additionally comprising the step of producing a compound of structural formula (5)

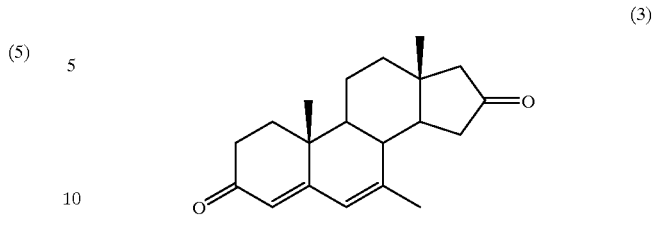

(5)

by treating a compound of structural formula (4):

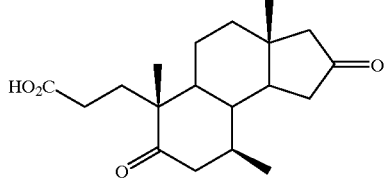

(4)

with sodium periodate and catalytic potassium permanganate and sodium carbonate, and isolating the resulting product (5).

8. The process according to claim 7, additionally comprising the step of producing a compound of structural formula (4):

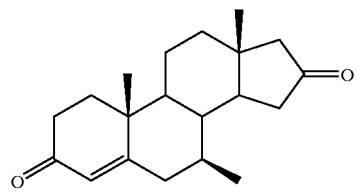

(4)

by treating a compound of structural formula (3):

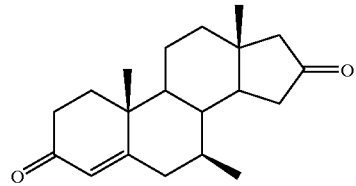

(3)

with 10% Pd/C, cyclohexene, and ethanol in an organic solvent, and isolating the resulting product (4).

9. The process according to claim 8, additionally comprising the step of producing a compound of structural formula (3):

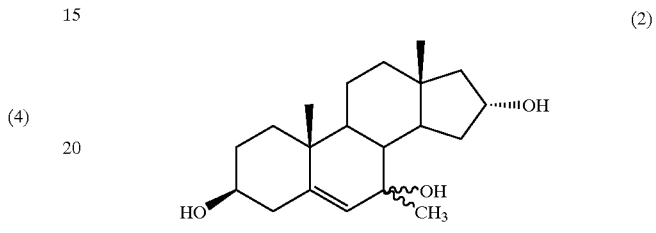

(3)

by treating a compound of structural formula (2):

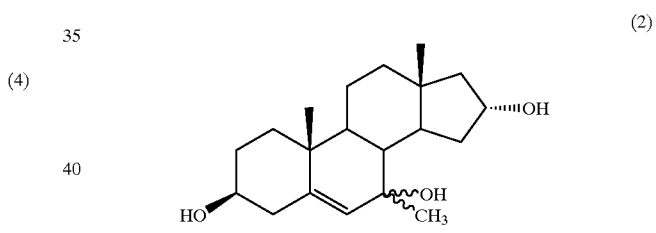

(2)

with aluminum isopropoxide and 2-butanone in the presence of organic base in an organic solvent, followed by addition of aqueous acid to the solution, neutralization with aqueous base and isolation of (3) as a solution in the organic solvent.

10. The process according to claim 9, additionally comprising the step of producing a compound of structural formula (2):

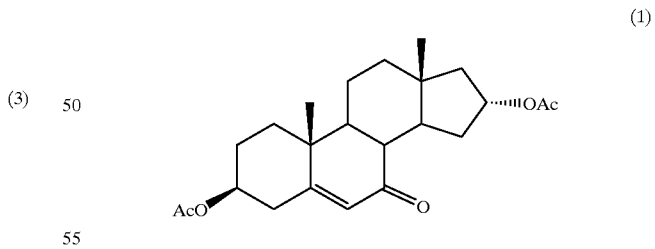

(2)

by treating a compound of structural formula (1):

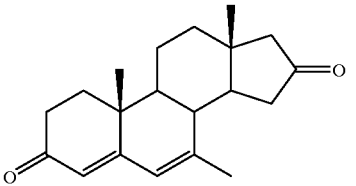

(1)

with methyl magnesium chloride in the presence of cerium chloride in an organic solvent.

11. The process according to claim 1 wherein Ar is selected from: unsubstituted or mono- or di-substituted phenyl, naphthyl, pyridyl, furyl, pyrrolyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl, and benzoxazolyl.

12. The process according to claim 11 additionally comprising the step of producing a compound of structural formula (10):

(10)

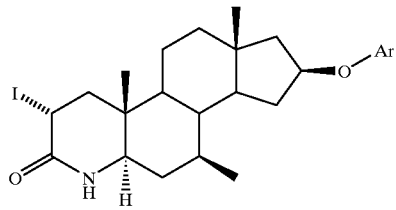

by treating a compound of structural formula (9):

(9)

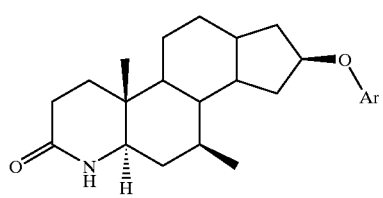

with trimethylsilyl chloride in the presence of an organic base and adding iodine, and isolating the resulting product (10).

13. The process according to claim 12 additionally comprising the step of producing a compound of structural formula (9)

(9)

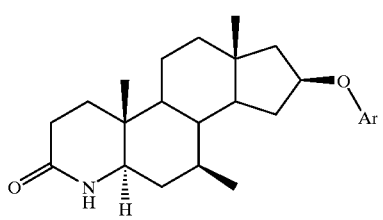

by treating a compound of structural formula (8):

(8)

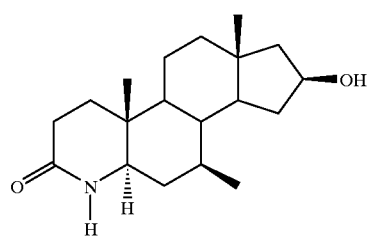

with potassium t-butoxide and adding Ar-F, and isolating the resulting product (9).

14. A process for producing a compound of structural formula (11):

(11)

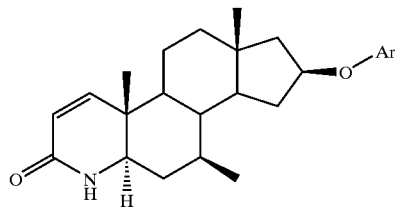

wherein:
Ar is an unsubstituted or mono- or di-substituted phenyl, naphthyl, or 5, 6 or 7 membered heteroaromatic ring containing at least one member selected from the group consisting of: one ring oxygen atom, one ring sulfur atom, 1–4 ring nitrogen atoms, or combinations thereof; in which the heteroaromatic ring can also be fused with one benzo or heteroaromatic ring;

comprising:
(a) by treating a compound of structural formula (1):

(1)

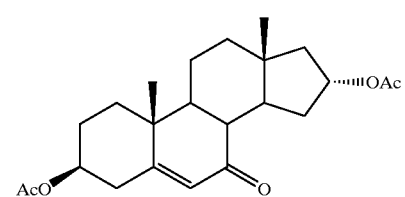

with methyl magnesium chloride in the presence of cerium chloride in an organic solvent to produce (2):

(2)

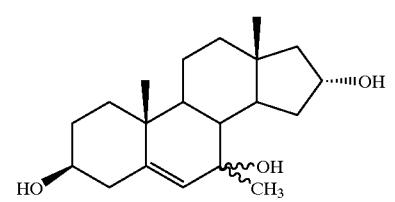

(b) treating the compound of structural formula (2) with aluminum isopropoxide and 2-butanone in the presence of organic base in an organic solvent, followed by addition of aqueous acid to the solution, neutralization with aqueous base and isolation (3) as a solution in the organic solvent:

(3)

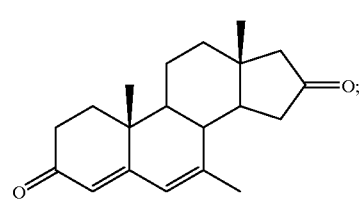

(c) treating the compound of structural formula (3) with 10% Pd/C, cyclohexene, and ethanol in an organic solvent, and isolating the resulting product (4):

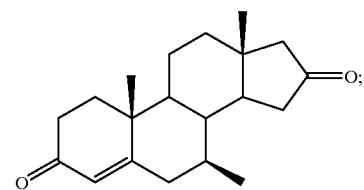

(4)

(d) treating the compound of structural formula (4) with sodium periodate and catalytic potassium permanganate and sodium carbonate, and isolating the resulting product (5):

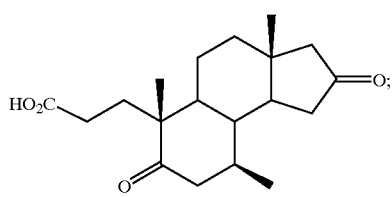

(5)

(e) treating the compound of structural formula (5) with ammonium acetate in refluxing acetic acid, and isolating the resulting product (6):

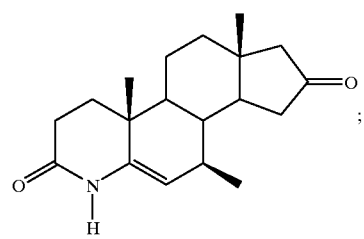

(6)

(f) treating the compound of structural formula (6) with lithium tri-sec-butylborohydride, followed by an oxidative workup, and and isolating the resulting product (7):

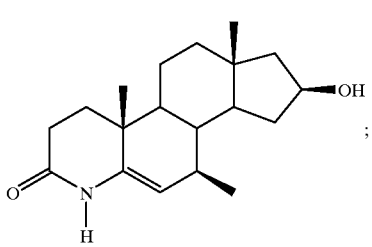

(7)

(g) hydrogenating the compound of structural formula (7) and isolating the resulting product (8):

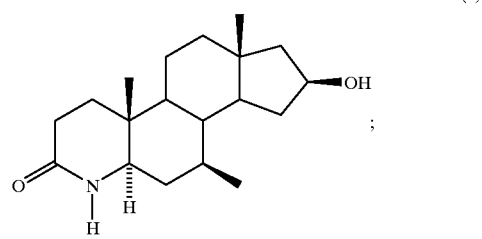

(8)

(h) treating the compound of structural formula (8) with potassium t-butoxide, adding Ar-F, and isolating the resulting product (9):

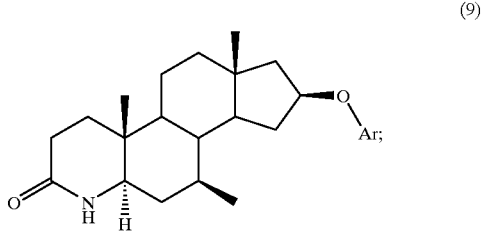

(9)

(i) treating the compound of structural formula (9) with trimethylsilyl chloride in the presence of an organic base and adding iodine, and isolating the resulting product (10):

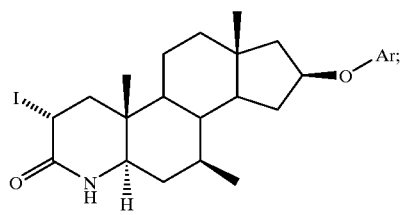

(10)

(i) treating the compound of structural formula (10) with potassium t-butoxide, and isolating the resulting product (11).

15. The process of claim 14 wherein Ar is 4-methylphenyl.

* * * * *